US008003397B2

(12) United States Patent
Wang et al.

(10) Patent No.: US 8,003,397 B2
(45) Date of Patent: Aug. 23, 2011

(54) GLUCOSE MONITORING BY VISCOMETRIC SENSING OF POLYMERIC FLUID

(75) Inventors: Qian Wang, Columbia, SC (US); Siqi Li, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 12/361,825

(22) Filed: Jan. 29, 2009

(65) Prior Publication Data

US 2009/0191642 A1    Jul. 30, 2009

Related U.S. Application Data

(60) Provisional application No. 61/062,732, filed on Jan. 29, 2008.

(51) Int. Cl.
*G01N 33/00* (2006.01)
(52) U.S. Cl. .............. 436/95; 436/94; 422/68.1; 422/73
(58) Field of Classification Search ........ 436/95
See application file for complete search history.

(56) References Cited

U.S. PATENT DOCUMENTS
2006/0089265 A1* 4/2006 Hanes et al. ........ 507/203

OTHER PUBLICATIONS

Li et al. (Li S.; Anderson, J.; Wang, Q. "Synthesis and Preparation of a Novel Glucose Sensing Fluid," ACS Southeastern Regional Meeting (SERMACS), Greenville, SC, Oct. 24-27, 2007, see entry No. 34 on p. 4).*

Kitano et al. ("Glucose-responsive complex formation between poly(vinyl alcohol) and poly(N-vinyl-2-pyrrolidone) with pendent phenylboronic acid moieties," Makromol. Chem., Rapid Commun. 1991, 12, 227-233).*
Shiomori et al. ("Thermoresponsive Properties of Sugar Sensitive Copolymer of N-Isopropylacrylamide and 3-(Acrylamido)phenylboronic Acid," Macromol. Chem. Phys. 2004, 205, 27-34.).*
Gabai et al. ("Characterization of the Swelling of Acrylamidophenylboronic Acid-Acrylamide Hydrogels upon Interaction with Glucose by Faradaic Impedance Spectroscopy, Chronopotentiometry, Quartz-Crystal Microbalance (QCM), and Surface Plasmon Resonance (SPR) Experiments," J. Phys. Chem. B 2001, 105, 8196-8202).*
Kuzimenkova et al. ("Boronate-Containing Copolymers: Polyelectrolyte Properties and Sugar-Specific Interaction with Agarose Gel," Macromol. Biosci. 2006, 6, 170-178.).*
Kitano et al. ("A novel drug delivery system utilizing a glucose responsive polymer complex between poly(vinyl alcohol) and poly(N-vinyl-2-pyrrolidone) with a phenylboronic acid moiety," Journal of Controlled Release 1992, 19, 162-170).*
Alexeev et al. "High Ionic Strength Glucose-Sensing Photonic Crystal," Anal. Chem. 2003, 75, 2316-2323.*

(Continued)

*Primary Examiner* — Yelena G Gakh
*Assistant Examiner* — Michelle M Adams
(74) *Attorney, Agent, or Firm* — Dority & Manning, P.A.

(57) ABSTRACT

A polymeric sensing fluid for detecting the presence of glucose and systems and methods of its use are generally disclosed. The polymeric sensing fluid includes a polymer in a solvent (e.g., an aqueous solvent). The polymer has a plurality of boronic acid moieties extending from its polymeric backbone. As such, the polymeric sensing fluid is configured to increase in viscosity upon addition of glucose due to crosslinking between the boronic acid moieties of the polymer and glucose.

8 Claims, 5 Drawing Sheets

OTHER PUBLICATIONS

Arnold et al., A membrane-moderated, conductimetric sensor for the detection and measurement of specific organic solutes in aqueous solutions, *Journal of Membrane Science* 167, 2000, pp. 227-239.

Asher et al., Photonic Crystal Carbohydrate Sensors: Low Ionic Strength Sugar Sensing, *J. Am. Chem.*, vol. 125, No. 11, 2003, pp. 3322-3329.

Diem et al., Clinical Performance of a Continuous Viscometric Affinity Sensor for Glucose, *Diabetes Technology & Therapeutics*, vol. 6, No. 6, 2004, pp. 790-799.

Enker et al., Augmentation of Tumor-Specific Immunogenicity by Concanavalin A in the Morris Hepatoma 5123, *Journal of Surgical Research*, vol. 16, No. 1, Jan. 1974, pp. 66-68.

Fang et al., Progress in Boronic Acid-Based Fluorescent Glucose Sensors, *Journal of Fluorescence*, vol. 14, No. 5, Sep. 2004, pp. 481-489.

Hawkins et al., The Reaction of o-(Bromomethyl)benzeneboronic Anhydride with Primary Amines, *J. Org. Chem.*, vol. 32(3), Mar. 1967, pp. 597-600.

Hegedus et al., Palladium-Assisted Cyclization-Insertion Reactions. Synthesis of Functionalized Heterocycles, *Journal of the American Chemical Society*, 102:10, May 7, 1980, pp. 3583-3587.

Ivanov, et al., "Synthesis of boronate-containing copolymers of N,N-dimethylacrylamide, their interaction with poly(vinyl alcohol) and rheological behaviour of the gels", Polymer, vol. 45 (2004), pp. 2495-2505.

Kataoka et al., Immunogenicity and Amplifier Cell Production by Tumor Vaccines Enhanced by Concanavalin A, *Gann*, 73, Apr. 1982, pp. 193-205.

Kitano et al., Interfacial Recognition of Sugars by Novel Boronic Acid-Carrying Amphiphiles Prepared with a Lipophilic Radical Initiator, *Langmuir*, vol. 14, No. 1, 1998, pp. 165-170.

Kuivila et al., Areneboronates from Diols and Polyols, *J. Org. Chem.*, 19 (5), 1954, pp. 780-783.

Kuzimenkova et al., Boronate-Containing Copolymers: Polyelectrolyte Properties and Sugar-Specific Interaction with Agarose Gel, *Macromol. Biosci.*, 6, 2006, pp. 170-178.

Lei et al., A Hydrogel-Based Implantable Mirocmachined Transponder for Wireless Glucose Measurement, *Diabetes Technology & Therapeutics*, vol. 8, No. 1, 2006, pp. 112-122.

Lorand et al., Polyol Complexes and Structure of the Benzeneboronate Ion, *J. Org. Chem.*, 24 (6), Jun. 1959, pp. 769-774.

Erna Möller, Contact-Induced Cytotoxicity by Lymphoid Cells Containing Foreign Isoantigens, *Science, New Series*, vol. 147, No. 3660, Feb. 19, 1965, pp. 873-874 and 879.

Yan et al., Boronolectins and Fluorescent Boronolectins: An Examination of the Detailed Chemistry Issues Important for the Design, *Medicinal Research Reviews*, vol. 25, No. 5, 2005, pp. 490-520.

Yang et al., Boronic Acid Compounds as Potential Pharmaceutical Agents, *Medicinal Research Reviews*, vol. 23, No. 3, 2003, pp. 346-368.

Zhao et al., A MEMS viscometric sensor for continuous glucose monitoring, *Journal of Micromechanics and Microengineering*, 17, 2007, pp. 2528-2537.

Phillips et al., Abstract of Lectin-dependent and anti-CD3 induced cytotoxicity are preferentially mediated by peripheral blood cytotoxic T lymphocytes expressing Leu-7 antigen, *The Journal of Immunology*, vol. 136, Issue 5, 1986, pp. 1579-1585.

CDC Diabetes, National Diabetes Fact Sheet, United States, 2005, General Information, 10 pages.

Information Sheet from Medtronic—Introducing the Guardian® REAL-Time Continuous Glucose Monitoring System, 2009, 3 pages.

Information Sheet from Medtronic—MiniMed Paradigm® REAL-Time Insulin Pump and Continuous Glucose Monitoring System, 2009, 2 pages.

* cited by examiner

GLUCOSE MONITORING BY VISCOMETRIC SENSING OF POLYMERIC FLUID

PRIORITY INFORMATION

The present application claims priority to U.S. Provisional Patent Application Ser. No. 61/062,732 filed on Jan. 29, 2008, which is incorporated by reference herein.

GOVERNMENT SUPPORT CLAUSE

The present invention was developed with funding from National Science Foundation grant number ECCS-0702056. The government may retain certain rights in the invention.

BACKGROUND OF THE INVENTION

Diabetes can cause premature death and serious long-term complications. Monitoring the blood sugar level is one of the important steps to control the disease and lower the risks of complications. Currently, the most commercially successful continuous glucose concentration monitoring system is implantable CGMS™ from Minimed (Northridge, Calif.). However, there are several drawbacks about this enzyme glucose oxidase based electrochemical device. The sensing is irreversible due to the consumption of glucose, insensitive because of limited diffusion resulting from the affinity of cells and other biomolecules, and inaccurate due to its side production of hydrogen peroxide and other electrode active chemicals.

A microelectromechanical systems (MEMS) viscometric sensor device for continuous glucose monitoring, using Dextran and Con A as the sensing fluid, has previously been developed. For example, the commercial system, GlucOnline® (Roche Diagnostics GMBH) has a sensing fluid based on Dextran/Concanavalin A and allows for stable test signals and low-decay measurement. The sensing fluid is known to have significant drawbacks such as immunotoxicity, cytotoxicity and instability.

In general, boronic acids are biocompatible functional groups with low cytotoxicities and low immunogenicity. As shown in scheme 1, boronic acid binds reversibly to diols to form a cyclic boronate ester:

Scheme 1: Interaction of boronic acid and diols.

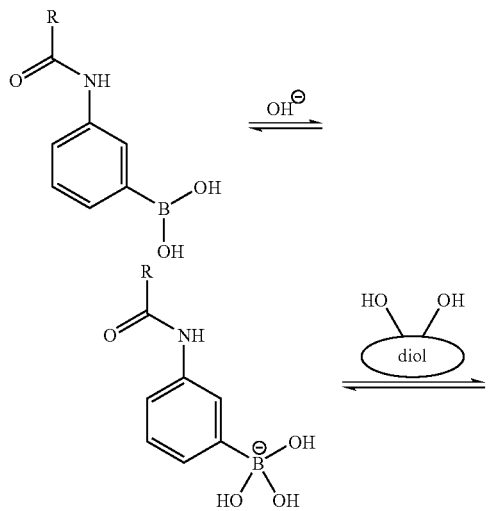

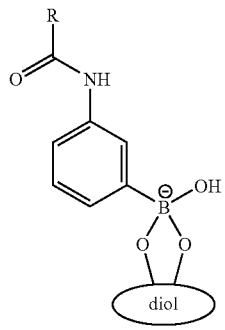

The binding causes photoelectron transfer or fluorescence resonance energy transfer or internal charge change that has been used to build fluorescent sensors. Asher, et al. have introduced the use of a polymerized crystalline colloidal array for calorimetric detection of glucose. See, Asher, S. A.; Alexeev, V. L.; Goponenko, A. V.; Sharma, A. C.; Lednev, I. K.; Wilcox, C. S.; Finegold, D. N. J. Am. Chem. Soc. 2003, 125, 3322-3329. Lei, et al. reported a swelling of the hydrogel due to the binding of glucose to the phenylborate group that was measured using a thin-film wireless pressure sensor. See, Lei, M.; Baldi, A.; Nuxoll, E.; Siegel, R. A.; Ziaie, B. Diabetes Technol. Therap. 2006, 8, 112-122. Arnold, et al. reported preliminary data from a conductimetric sensor with a boronic acid immobilized in a hydrogel, which was encapsulated in a bipolar ion exchange membrane impermeable to ions but freely permeable to glucose. See, Arnold, F. H.; Zheng, W. G.; Michaels, A. S. J. Membrane Sci. 2000, 167, 227-239. The change in ionic conductivity of the hydrogel resulting from the increase in ion concentration due to the binding of glucose to the boronic acid was measured with a pair of thin-film gold electrodes. However, there are intrinsic shortcomings with each type of those sensors. For example, fluorescence-based affinity sensors are inaccurate due to light intensity variations, the potential interference of other fluorescent biochemicals, and the requirement of relatively bulky and expensive optical instruments.

To address the drawbacks of the previous systems, a stable, biocompatible polymeric sensing fluid has been developed and is presently disclosed.

SUMMARY

Objects and advantages of the invention will be set forth in part in the following description, or may be obvious from the description, or may be learned through practice of the invention.

In general, the present disclosure is directed toward a polymeric sensing fluid for detecting the presence of glucose and systems and methods of its use. The polymeric sensing fluid includes a polymer in a solvent (e.g., an aqueous solvent). The polymer has a plurality of boronic acid moieties extending from its polymeric backbone. As such, the polymeric sensing fluid is configured to increase in viscosity upon addition of glucose due to crosslinking between the boronic acid moieties of the polymer and glucose.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

DETAILED DESCRIPTION

Figure 1:
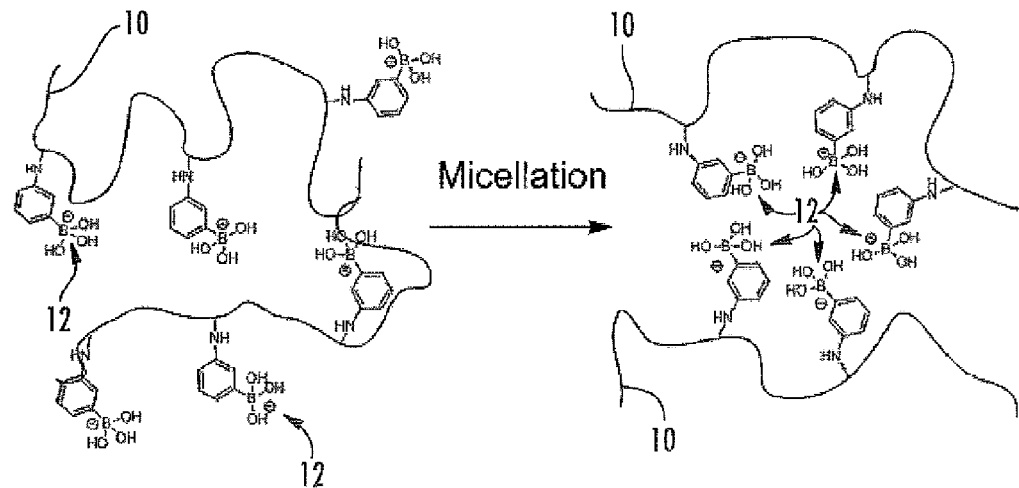
FIG. 1 shows an exemplary mechanism of polymeric micelle formation of PAA-ran-PAAPBA.

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Generally speaking, the present invention is directed to a stable, biocompatible polymeric system for specific detection of glucose. In particular, a method and composition for a stable, biocompatible boronic acid based polymeric sensing fluid useful in a MEMS device is disclosed. The application of this sensing fluid to MEMS viscometric sensors allows for a highly reliable, continuous monitoring of glucose in interstitial fluid in subcutaneous tissue.

The sensing fluid of the present invention generally relies on the biocompatibility of boronic acids functional groups with low cytotoxicities and low immunogenicity, as shown in Scheme 1 above. Thus, the sensing fluid can form reversible bonds between the boronic acid functional groups and any glucose in the sample. These bonds can result in changes of the physical characteristics (e.g., the viscosity) of the polymeric sensing solution, which can be measured to extrapolate the presence and amount of glucose in the sample.

The sensing fluid of the present invention is generally a polymeric sensing system. A polymer having boronic acid functional groups extending from the polymeric backbone (i.e., the boronic acid moieties) can allow glucose to reversibly form ester bonds with boronic acid moiety. These bonds can result in cross-linking of the polymers in the system, which leads to an increase in the solution viscosity.

The viscosity of the polymeric sensing solution can become steady within minutes upon changing glucose concentrations. Additionally, the system can quickly reach equilibrium such that little change in the viscosity of the system can be seen, even after hours of sitting. The polymeric composition can be configured such that a viscosity increase can be observed when glucose concentration increases. For example, a viscosity increase can be observed when glucose concentration increases from 0 to 25 mM.

Through proper adjustment of the composition percentage of the boronic acid moieties on the polymer and polymer concentrations, the sensing fluids can detect and differentiate glucose from other monosaccharides and disaccharides. Thus, the polymeric sensing fluid can be highly specific response to glucose. Applying this fluid to a MEMS viscometric device will enable highly reliable, continuous monitoring of glucose in ISF in subcutaneous tissue.

The ester bonds can be broken to substantially recover the polymeric sensing fluid and/or the sample containing glucose. For example, dialysis of the glucose crosslinked polymeric sensing fluid using water and passing through a semipermeable membrane can result in significant decreases of viscosity. This decrease in viscosity is believed to be due to the loss of the ester bonds between the boronic acid moieties of the polymeric backbone and the glucose in the sample. As such, the polymeric sensing fluid may be recovered and reused to test other samples for the presence of glucose.

A. Polymers for the Sensing System

The polymeric sensing solution generally includes a polymer with boronic acid functional groups extending from a polymeric backbone. Through proper adjustment of the composition percentage of the boronic acid moieties on the polymer and the polymer concentration in the fluid, the polymeric sensing fluids can detect and differentiate glucose from other monosaccharides and disaccharides.

In one particular embodiment, a suitable polymer having boronic acid moieties can be formed as a copolymer of at least two monomers, where one of the monomers includes at least one boronic acid functional group. A copolymer can be synthesized with these monomers via classic free radical copolymerization processes.

Monomers having at least one boronic acid functional group can generally be represented by the generic formula:

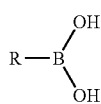

Formula I

Boronic Acid Moiety where R contains a polymerizeable carbon group.

In one particular embodiment, the monomer having at least one boronic acid functional group have a phenylboronic acid moiety, such as represented by the generic formula:

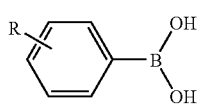

Formula II

Phenylboronic Acid Moiety where R is shown in short-hand to be bonded at any position on the phenyl ring (e.g., assuming the boronic acid group is at position 1, then the R group can be at any of the 2, 3, 4, 5, or 6 positions on the 6-carbon ring). Also, more than one R group may be present on the phenyl ring. In one particular embodiment, the R group is positioned adjacent to the boronic acid group on the phenyl ring (i.e., at position 2), as represented below:

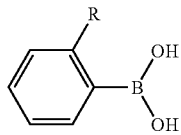

Formula III

2-Phenylboronic Acid Moiety (or Ortho-Phenylboronic Acid Moiety)

In one embodiment, the phenylboronic acid moiety can have an R group can include a secondary amine in the carbon chain. For example, the phenylboronic acid moiety can be an ortho-, meta-, or para-aminophenylboronic acid, or an ortho-aminomethylphenylboronic acid, such as represented by the following formulas:

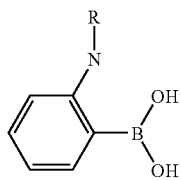

Formula IV

Ortho-Aminophenylboronic Acid;

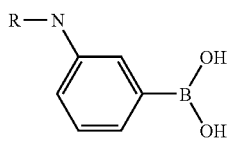

Formula V

Meta-Aminophenylboronic Acid;

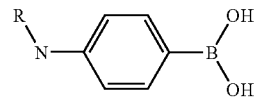

Formula VI

Para-Aminophenylboronic Acid Moiety; and

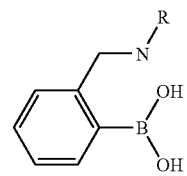

Formula VII

Ortho-Aminomethylphenylboronic Acid

The ortho-aminomethylphenylboronic acid moiety (shown in Formula VIII) is particularly useful to form the polymeric sensing fluid due. The ortho-positioning may improve the ability of the boronic acid moiety to interact with the diol. Without wishing to be bound by theory, it is believed that interactions between the amino group (e.g., the hydrogen bonded to the nitrogen and/or the unbonded electron pair on the nitrogen and/or oxygen atoms) and the boron of the boronic acid group can facilitate the formation of a cyclic boronate ester when reacting with a diol such as glucose in the presence of hydroxide anions. Specifically, it is believed that interaction between the electron pair of the nitrogen atom of the amino group and the boron in close proximity to the phenyl group can conjugate to form a second conjugated ring-like structure adjacent to the phenyl group to spread the negative charge formed on the boron created during the reaction shown in Scheme 1 in bonding to a diol.

In all of the above shown formulas, R represents a polymerizable carbon chain. For example, the polymerizeable carbon chain (R) can include, in one particular embodiment, an acrylic or methacrylic group (i.e., R can be a carbon chain ending in an acryloyl group or a methacryloyl group). An acryloyl group is the functional group with structure $H_2C=CH-C(=O)-R$. Thus, the monomer having at least one boronic acid functional group attached to an acryloyl group can have the following generic formula:

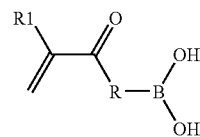

Formula VIII

Boronic Acid Moiety Linked to an Acryloyl Group where R1 is either H or CH₃ (forming an acryloyl group or a methacryloyl group, respectfully) and R contains a carbon chain or ring.

In one particular embodiment, the monomer having at least one boronic acid functional group linked to an acryloyl group or a methacryloyl group can further include an amine group. When the amine group is positioned adjacent to the acryloyl group or methacryloyl group, the group can be referred to as an acrylamide group or methacrylamide group, respectfully. Thus, the monomer having at least one boronic acid functional group linked to an acrylamide group can be represented by the formula:

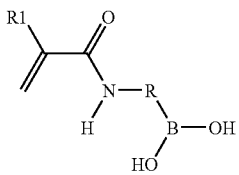

Formula IX

Boronic Acid Moiety Linked to an Acrylamide Group where R1 is either H or CH₃ (forming acrylamide or methacrylamide, respectfully) and R is a carbon chain or ring.

For example, monomers having a phenylboronic acid moiety linked to an acrylamide or methacrylamide group via a carbon chain can be generically referred to as an acrylamidophenylboronic acid, which can be represented by the formula:

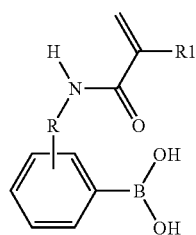

Formula X

Phenylboronic Acid Moiety Linked to an Acrylamide Group where R is a covelant bond or contains a carbon chain or ring, and can be bonded to any available position on the phenyl ring. One simple example of a phenylboronic acid moiety linked to an acrylamide group (where R is simply a covalent bond) is N-3-acrylamidophenylboronic acid (AAPBA), such as represented by the formula:

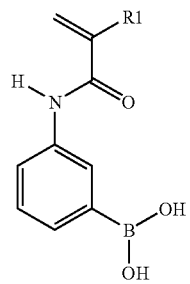

Formula XI

N-3-Acrylamidophenylboronic Acid

The monomer N-3-acrylamidophenylboronic acid can be formed by reacting 3-aminophenylboronic acid with acryloyl chloride in an aqueous solution containing hydroxide (e.g., NaOH), such as described in Example 1 below. This reaction can be represented according to the following reaction shown in Scheme 2:

Scheme 2: Formation of N-3-Acrylamidophenylboronic Acid

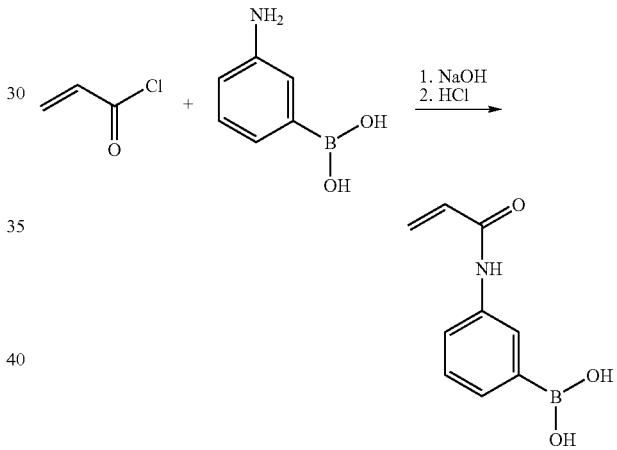

In one particular embodiment, the linking R group can be positioned at the 2 position on the phenyl ring, as represented below:

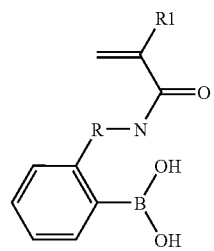

Formula XII

Ortho-Phenylboronic Acid Moiety Linked to an Acrylamide Group

When the phenylboronic acid moiety is linked to an acrylamide or methacrylamide group via a carbon chain containing an amine (e.g., a secondary amine) at the 2 position, one particular embodiment of such a compound can be generically represented by the formula:

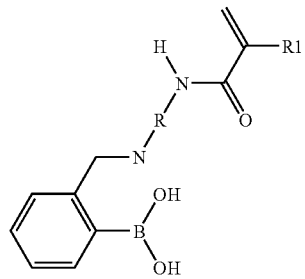

Formula XIII

Ortho-Aminomethylphenylboronic Acid linked to an Acrylamide Group

Specific examples of suitable combinations of phenylboronic acid moieties linked to an acrylamide or methacrylamide group via the 2-position (i.e., ortho-position) on the phenyl ring include those monomers represented by the following formulas:

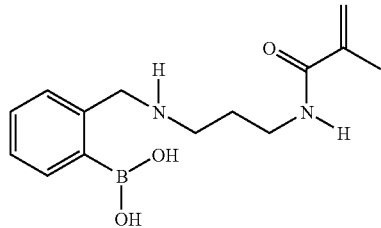

Formula XIV 2-((3-methacrylamidopropylamino)methyl)phenylboronic Acid;

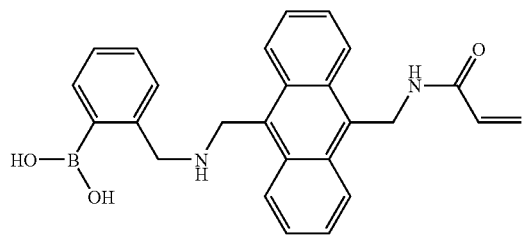

Formula XV (Z)-2-(((4-(acrylamidomethyl)-3-(prop-1-enyl)-2-vinylnaphthalen-1-yl)methylamino)methyl)phenylboronic Acid;

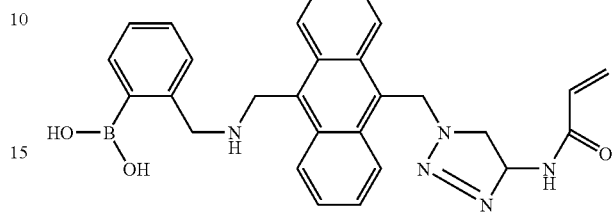

Formula XVI (Z)-2-(((4-((4-acrylamido-1H-1,2,3-triazol-1-yl)methyl)-3-(prop-1-enyl)-2-vinylnaphthalen-1-yl)methylamino)methyl)phenylboronic Acid;

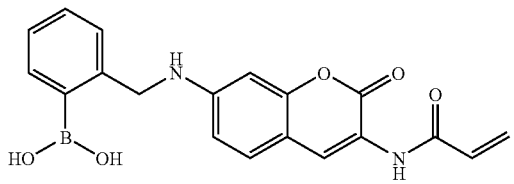

Formula XVII 2-((3-acrylamido-2-oxo-2H-chromen-7-ylamino)methyl)phenylboronic Acid; and

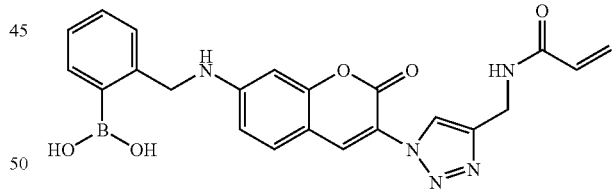

Formula XVIII 2-((3-(4-(acrylamidomethyl)-1H-1,2,3-triazol-1-yl)-2-oxo-2H-chromen-7-ylamino)methyl)phenylboronic Acid Other monomers containing a phenylboronic acid moiety linked to an acrylamide or methacrylamide group via a carbon chain (R) as shown in Formula IX can be prepared such that the R group incorporates various dyes or fluorophores including coumarin, fluorescein, rhodamine, anthracene, BODIPY and their derivatives. In this embodiment, the phenylboronic acid moiety can include an aminophenylboronic acid moiety such as ortho-, meta- and para-aminophenylboronic acid and ortho-aminomethylphenylboronic acid (all shown above in Formulas IV, V, VI, and VII, respectfully).

In one particular embodiment, the phenylboronic acid moiety is linked to the acrylamide or methacrylamide group according to the following formula:

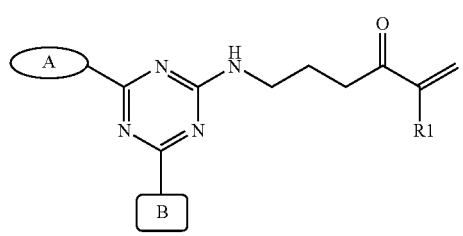

Formula XIX 1,3,5-triazine Based Monomers where R1 is H or CH$_3$ and where A is a fluorophore or dye function group linked via the amine group, such as the compounds represented by any of the following formulas:

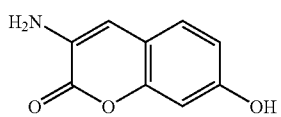

Formula XX 3-amino-7-hydroxycoumarin;

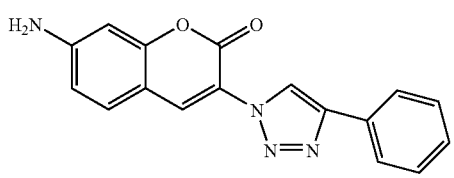

Formula XXI 7-amino-3-(4-phenyl-1H-1,2,3-triazol-1-yl)-2H-chromen-2-one;

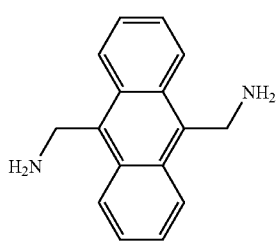

Formula XXII anthracene-9,10-diyldimethanamine;

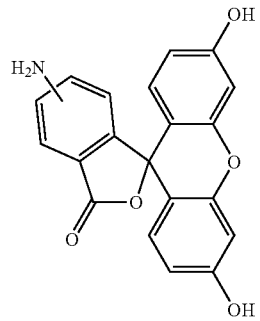

Formula XXIII

5/6-aminofluorescein; and

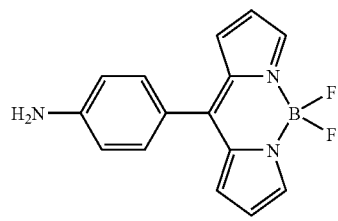

Formula XXIV

Boron, difluoro[4-[(1H-pyrrol-2-yl-κN)(2H-pyrrol-2-ylidene-κN)methyl]benzenaminato]-, (T-4)-;

and where B is a boronic acid moiety (such as ortho-, meta- and para-aminophenylboronic acid and ortho-aminomethylphenylboronic acid shown above in Formulas IV, V, VI, and VII, respectfully).

Any of the above monomers can be polymerized to form a polymer for use in the polymeric sensing fluid. The polymer can be a homopolymer (i.e., without any other monomer present in the polymeric backbone) or a copolymer with one or more other monomers. Thus, the use of the term "polymer" generically refers to a homopolymer and/or a copolymer.

For example, those monomers having an ortho-aminomethylphenylboronic acid linked to an acrylamide or methacrylamide group can be polymerized into a homopolymer (i.e., without the presence of another monomer in the polymeric backbone). Without wishing to be bound by theory, it is believed that the interactions between the nitrogen of the aminomethyl group and the boron of the boronic acid group adds stability to the functional group extending from the polymeric backbone.

The above monomers may also be polymerized with at least one other monomer to form a copolymer containing the boronic acid moieties as functional groups extending from the polymeric backbone. The other monomer(s) can be selected to control properties of the resulting copolymer. The other monomer(s) may be selected to control the solubility of the copolymer in a certain solvent (e.g., water). For example, the other monomer(s) may be selected to ensure that the copolymer is soluble in water or at least dispersible in water. Their solubility can be quantified via swelling experiments or turbidity titration or the group contribution method.

The monomer having the boronic acid moiety can be polymerized with any other suitable backbone monomer to form a copolymer suitable for the polymeric sensing solution. The backbone monomer can be, when the monomer having the boronic acid moiety contains an acrylic functionality, a monomer suitable for polymerization with an acrylic functional group (e.g., acrylic acid, methacrylic acid, acrylamide, methacrylamide, etc.). Other polymerizable monomers include those with vinyl groups (e.g., vinyl chloride, vinyl acetate, etc.); those with polymerizable hydroxyl groups (e.g., ethylene glycol, propylene glycol, etc.), epoxides, and other polymerizable monomers.

Boronic acid groups can also be grafted to an existing polymer backbone by 2-formalphenylboronic acid and amine group.

When the monomer including a boronic acid moiety is copolymerized with another monomer, the monomer including a boronic acid moiety can be present in any effective amount, such as from about 0.1% to about 12% by mole (e.g., by molar percent). The percent composition was calculated by the integration area ratio of the aromatic protons to methylene and methine protons using $^1$H NMR spectroscopy.

For example, N-3-acrylamidophenylboronic acid and acrylamide can be polymerized in the presence of 2,2'-azobisisobutyronitrile (AIBN) to form a copolymer, such as discussed in Example 1, according to the following formula:

Scheme 3: Polymerization of poly(acrylamide-ran-3-acrylamidophenylboronic acid)

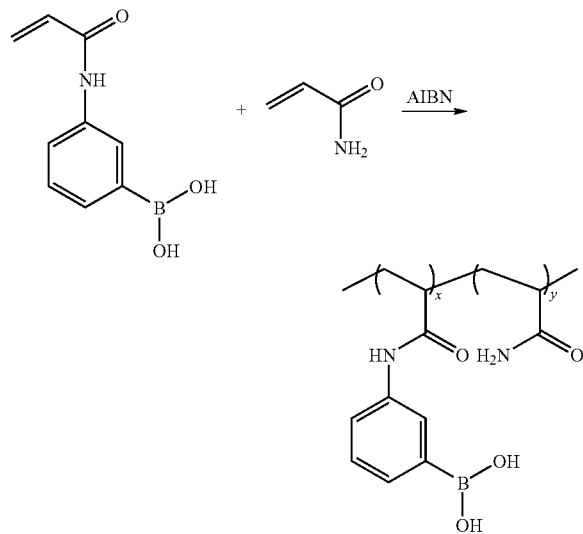

The resulting copolymer of this polymerization is poly(acrylamide-ran-3-acrylamidophenylboronic acid) (abbreviated "PAA-ran-PAAPBA"). The concentrations (x and y as shown in Scheme 3) of the two monomers can be varied as desired to control the properties of the resulting copolymer. The amount of the monomer N-3-acrylamidophenylboronic acid in this copolymer (i.e., "x" in Scheme 3) is limited due to solubility limitations of the copolymer in an aqueous solution. If the concentration of the monomer N-3-acrylamidophenylboronic acid is too high, the resulting copolymer may not be soluble in an aqueous solution, and therefore may not be suitable for use in a polymeric sensing fluid.

In most embodiments, the monomer N-3-acrylamidophenylboronic acid can be present in the copolymer from about 0.1% to about 10% by mole (i.e., about $0.1\% \geq x \geq$ about 10%), such as from about 0.5% to about 8% by mole. In one particular embodiment, the monomer N-3-acrylamidophenylboronic acid can be present in the copolymer from about 1% to about 6% by mole (i.e., about $1\% \geq x \geq$ about 6%), such as from about 2% to about 5% by mole. Thus, the acrylamide monomer can be present in the copolymer from about 90% to about 99.9% by mole (i.e., about $90\% \geq y \geq$ about 99.9%), such as from about 92% to about 99.5% by mole. In one particular embodiment, the acrylamide monomer can be present in the copolymer from about 94% to about 99% by mole (i.e., about $94\% \geq y \geq$ about 99%), such as from about 95% to about 98% by mole.

In one particular embodiment, an initiator may be present, such as AIBN, to facilitate polymerization. The initiator can be present in the copolymer, in one embodiment, up to about 1% by mole, such as from about 0.1% to about 0.5% by mole, compared to the amount of monomer having the boronic acid moiety (by mole). For example, AIBN can be present from about 0.1% to about 1% of the molar amount of the monomer having the boronic acid moiety.

The polymeric sensing fluid can be an aqueous solution containing the polymer dissolved or dispersed in water. Of course, any other suitable solvents can be used.

Additionally, other components can be included within the polymeric sensing fluid, including, but not limited to, buffers, preservatives, surfactants, etc.

Without wishing to be bound by theory, it is believed that the polymer containing the boronic acid moieties forms micelles in the polymeric solution. For example, FIG. 1 shows micelles being formed in the polymeric sensing solution with the polymer includes the monomer N-3-acrylamidophenylboronic acid. The polymeric backbone 10 has boronic acid moieties 12 extending from the polymeric backbone 10.

B. Detecting the Presence of Glucose

The boronic acid moieties on the polymer of the polymeric sensing fluid of the present invention can react with glucose to effectively crosslink the polymer in the fluid. This crosslinking occurs according to the reaction of the boronic acid moieties on the polymer and the diols of the glucose molecule. Specifically, the hydroxyl groups on the glucose molecules can form reversible bonds with the boronic acid moieties of the polymer, as shown in Scheme 4:

Scheme 4: Interaction of phenylboronic acid and D-glucose.

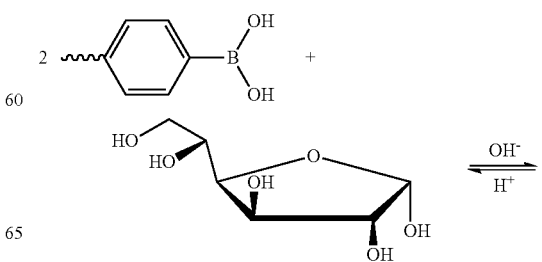

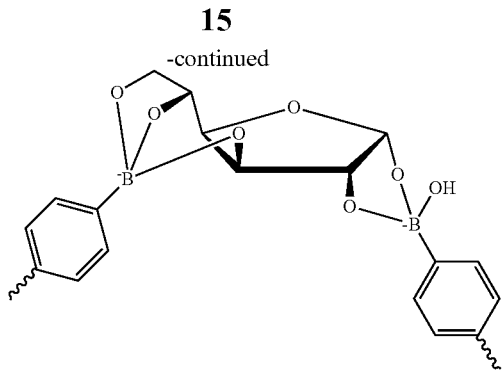

Figure 2A:
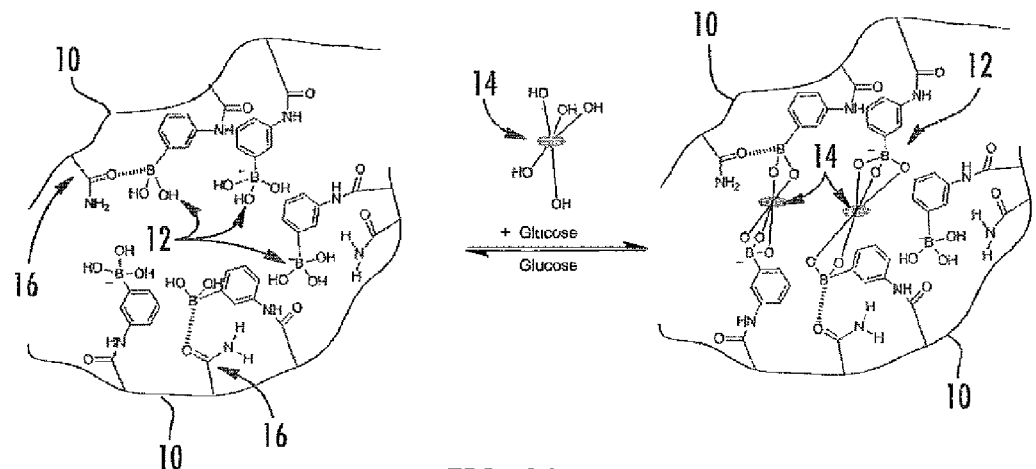
FIGS. 2a and 2b show exemplary mechanisms of glucose cross-linking of PAA-ran-PAAPBA.
Figure 2B:
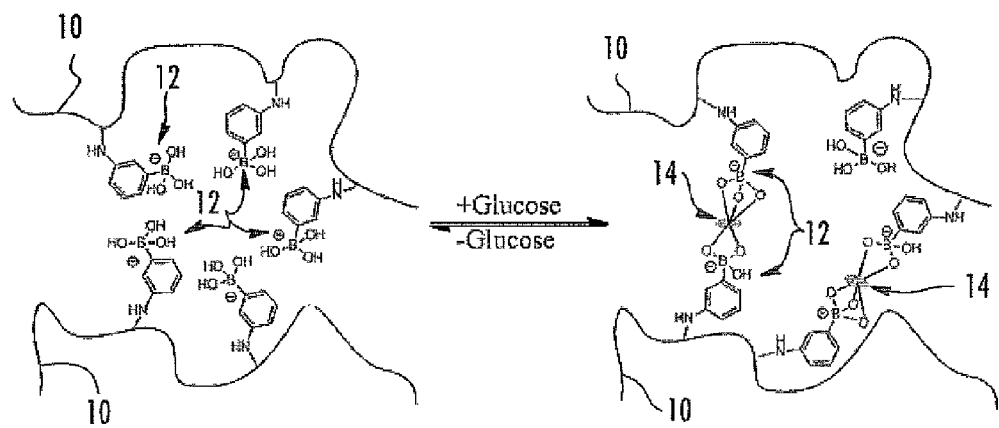

For example, FIGS. 2a and 2b show crosslinking in an exemplary polymeric solution when the polymer in the polymeric sensing fluid includes the monomer N-3-acrylamidophenylboronic acid. The polymeric backbone 10 has boronic acid moieties 12 (in the form of meta-aminophenylboronic acid moieties) extending from the polymeric backbone 10 (e.g., a polyacrylate backbone such as polyacrylamide). The addition of glucose to the polymeric solution causes crosslinking between boronic acid moieties 12 through the glucose molecules 14. FIG. 2a shows that the inclusion of acrylamide in forming a copolymer may facilitate crosslinking with glucose due to interaction between the oxygen and/or nitrogen on the acrylamide groups 16 of the polymer backbone 10.

These bonds effectively crosslink the polymeric material in the polymeric sensing fluid and causes the viscosity of the fluid to increase. The degree of the change in viscosity caused by this crosslinking can vary depending on the particular polymer and its concentration in the polymeric sensing fluid, and the concentration of the glucose.

An increase in the viscosity of the fluid can be measured according to any suitable method to indicate the presence of glucose. For example, commercially available viscometers and viscometric devices can quantify the viscosity of a fluid.

The polymeric sensing fluid of the present invention can be used in any suitable sensing device. For example, the polymeric sensing fluid of the present invention can be substituted for the Dextran/Concanavaline A based sensing fluid for use in the MEMS device commercially available under the trade name GlucOnline® (Roche Diagnostics GMBH).

Figure 3:
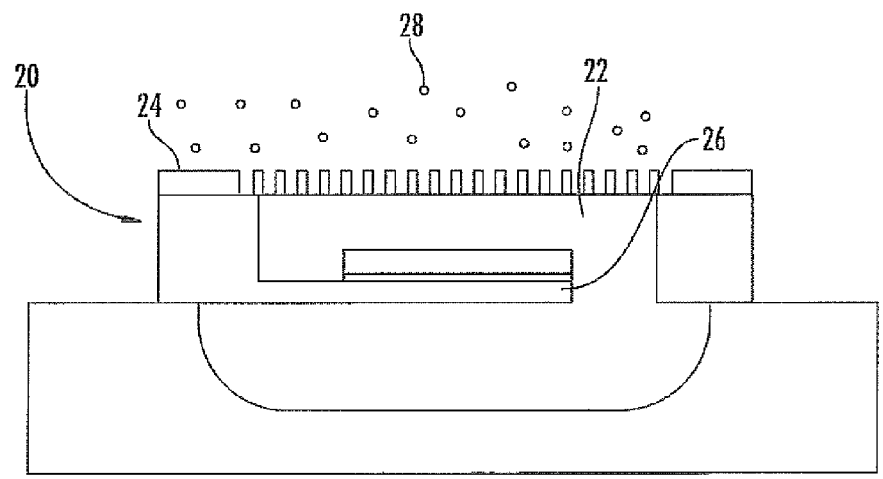
FIG. 3 shows a schematic illustration of the MEMS viscometric device.

FIG. 3 shows an exemplary MEMS viscometric device 20 containing a polymeric sensing fluid 22. The polymeric sensing fluid 22 contains the polymer having a plurality of boronic acid moieties in a solvent (e.g., water) to form a solution or dispersion. The MEMS viscometric device 20 includes a semi-permeable membrane 24 separating the polymeric sensing fluid 22 and the glucose molecules 28. A cantilever 26 is also included in the MEMS viscometric device 20 to detect changes in the viscosity of the polymeric sensing fluid 22 through vibrations. Of course, other configurations for MEMS viscometric devices suitable for use with the presently disclosed polymeric sensing fluid can be utilized in accordance with the present invention.

EXAMPLES

The following experiments are provided to illustrate the present invention and are not intended to limit the scope of the invention. These experimental results show that the viscosity values of an exemplary polymeric sensing fluid can become steady within minutes upon changing glucose concentrations and with little changes even after hours, indicating that the system quickly reaches equilibrium. Through adjustment of the composition percentage of the boronic acid monomer in the copolymer, a nearly five-fold viscosity increase was observed when glucose concentration increased from 0 to 25 mM, which was strong enough to be detected by a MEMS device (testing performed by Dr. Qiao Lin, Columbia University). After dialysis of the mixture against water through a semi-permeable membrane, significant decreases of viscosity were observed at different time scales, suggesting that the response of the fluid to glucose concentrations was reversible. Moreover, this sensing fluid has shown a highly specific response to glucose.

Materials. 3-Aminophenylboronic acid (PBA) was purchased from Oakwood Products, Inc. SnakeSkin™ Pleated Dialysis Tubing (MWCO 3500) was purchased from Pierce Biotechnology, Inc. Ubbelohde viscometer was obtained from CANNON® Instrument Company. All other reagents, including D-(−)-fructose, D-(+)-glucose, D-(+)-lactose, D-(+)-galactose, D-(+)-sucrose, D-(+)-cellobiose, D-(+)-mannose, PEG8000, sodium azide, sodium chloride, potassium phosphate monobasic, and potassium phosphate dibasic, were purchased from Sigma-Aldrich, Inc (St. Louis, Mo.). Nanopure water was purified by Milli-Q Ultrapure system purchased from Millipore Corporation (Billerica, Mass.).

Preparation of Monomer
N-3-acrylamidophenylboronic Acid (AAPBA)

The monomer AAPBA was synthesized adopting conditions similar to those disclosed in Ivanov, A. E.; Larsson, H.; Galaev, I. Y.; Mattiasson, B. *Polymer*, 2004, 45, 2495-2505, which is incorporated by reference herein to the extent it does not conflict with the present disclosure. However, the AAPBA was prepared in a yield higher than those found in the above reference using a modified protocol where more product was recovered using ethyl acetate to extract the acidic aqueous filtrate. 3-Aminophenylboronic acid (5 g, 36.5 mmol) was dissolved in NaOH solution (2 M, 73 mL, 146 mmol) at 0° C. Cold acryloyl chloride (5.9 mL, 73 mmol) was added dropwisely to the vigorously stirred mixture over 15 min. HCl solution (1 M) was slowly added to the reaction mixture till the pH reached 1.0. A lot of white solids precipitated, which were filtered, washed by cold water. The filtrate was extracted with EtOAc three times. The organic phase was washed with brine and evaporated to give off-white solids which were combined with the above precipitates. Recrystallization in $H_2O$ afforded 5.0 g off-white AAPBA crystals (yield: 72%). The $^1H$ NMR and $^{13}C$ NMR spectra were recorded on a Mercury VX-300 spectrometer (Varian, USA). $^1H$ NMR (300 MHz, DMSO-$d_6$): δ=10.06 (s, 1H, O=CNH), 8.01 (s, 2H, B—OH), 7.87 (s, 2H, Ar—H), 7.81 (d, J=8.1 Hz, 1H; Ar—H), 7.49 (d, J=7.2 Hz, 1H; Ar—H), 7.27 (t, $J_1$=7.5 Hz, $J_2$=7.8 Hz, 1H; Ar—H), 6.44 (dd, J=16.8 Hz, $J_2$=9.9 Hz, 1H; C=CHC=O), 6.23 (dd, $J_1$=17.1 Hz, $J_2$=2.1 Hz, 1H, C=$CH_2$), 5.72 (dd, $J_1$=9.9 Hz, $J_2$=2.1 Hz, 1H; C=$CH_2$). $^{13}C$ NMR (75.5 MHz, DMSO-$d_6$): δ=163.8, 138.8, 135.6, 132.7, 130.0, 128.4, 127.3, 126.0, 122.0.

Preparation of Control Monomer
N-Phenylacrylamide (NPAA)

Control monomer, NPAA, was prepared as reported with a similar yield in Hegedus, L. S.; Allen, G. F.; Olsen, D. J. *J. Am. Chem. Soc.* 1980, 102, 3583-3587. $^1H$ NMR (300 MHz, $CDCl_3$): δ=7.58 (d, $J_1$=8.1 Hz, 2H; ArH), 7.51 (s, 1H, O=CNH), 7.37 (d, J=1.8 Hz, 1H, Ar—H), 7.32 (t, $J_1$=6.6 Hz, $J_2$=1.8 Hz, 1H, Ar—H), 7.13 (t, $J_1$=7.5 Hz, $J_2$=7.2 Hz, 1H; Ar—H), 6.44 (dd, $J_1$=16.8 Hz, $J_2$=1.5 Hz, 1H; C=CH$_2$), 6.24 (dd, $J_1$=16.8 Hz, $J_2$=10.2 Hz, 1H; C=CHC=O), 5.78 (dd, J=10.5 Hz, $J_2$=1.5 Hz, 1H; C=CH$_2$). $^{13}$C NMR (75.5 MHz, CDCl$_3$): δ=164.4, 138.1, 131.6, 129.2, 127.9, 124.8, 120.6.

Preparation of the Copolymer PAA-ran-AAPBA

A copolymer poly(acrylamide-ran-3-acrylamidophenyl-boronic acid) (PAA-ran-AAPBA) was synthesized through classic free radical solution polymerization conducted as following: acrylamide (3.72 g, 52.4 mmol), AAPBA (0.20 g, 1 mmol) and 2,2'-azodiisobutyronitrile (AIBN, 21.5 mg, 0.13 mmol) were dissolved in DMSO. The mixture was bubbled by nitrogen for half an hour, and subjected to 70° C. oil bath for 24 h. After cooling down to room temperature, the gel was subjected to dialysis against nanopure water for 24 h. The aqueous phase was precipitated by acetone (ten fold volume) twice and dried in vacuum oven to give 3.07 g white solids (Yield: 78%).

A series of copolymers with different percent compositions were prepared and characterized by $^1$H NMR in D$_2$O, $^{11}$B NMR and viscometry. $^1$H NMR (300 MHz, D$_2$O) for a typical polymer: δ=7.41 (bm, 4H; ArH), 2.06 (bm, 1H, O=CCH—), 1.50 (bm, 2H, —CH$_2$—). The presence of trigonal boron in the polymer using solid state $^{11}$B NMR technique was confirmed by the presence of a broad peak centered at δ 25 ppm. The $^{11}$B NMR spectrum of solid-state polymer was recorded on a Varian Inova 500 spectrometer at 160.5 MHz (Varian, USA) using Doty XC-4 mm MAS probe. Bloch decays were collected using $^1$H dipolar decoupling and a spinning rate of 10 kHz. $^{11}$B NMR (160.5 MHz, solid) for a typical polymer: δ=25 ppm (a broad peak).

Control polymer polyacrylamide-ran-N-phenylacrylamide (PAA-ran-PNPAA) was prepared and characterized in the similar way. $^1$H NMR (300 MHz, D$_2$O): δ=7.3 (bm, 5H; ArH), 2.07 (bm, 1H, O=CCH—), 1.50 (bm, 2H, —CH$_2$—).

Due to the possible binding between boronic acid and polar stationary phase like silica of aqueous gel permeation chromatography, their weight-average molecular weight were calculated based on their intrinsic viscosities obtained under similar conditions used by Kuzimenkova, M. V.; Ivanov, A. E.; Galaev, I. Y. Macromol. Biosci. 2006, 6, 170-178. Because the polymers were polyacrylamide analogs, the Mark-Houwink parameters for polyacrylamide were used in the calculation. A variety of free radical polymerization conditions were tested, among which it was discovered that the polymer molecular weight was not under direct control by the ratio of initiator to monomers (see Table 1). It was observed that using 0.25 molar ratio of the initiator to acrylamide gave the best results with reproducible copolymer composition and higher molecular weight. The final percent composition of PAAPBA segment could be determined by $^1$H NMR through the integration ratio of the aromatic protons to methylene and methine protons, which was fairly consistent with the initial molar ratio before polymerization (Table 1). However, when the molar ratio of AAPBA to acrylamide was more than 8:100 in the monomer mixture, it was very difficult to generate polymers with high molecular weights, likely due to the low solubility of the final polymers.

Figure 4A:
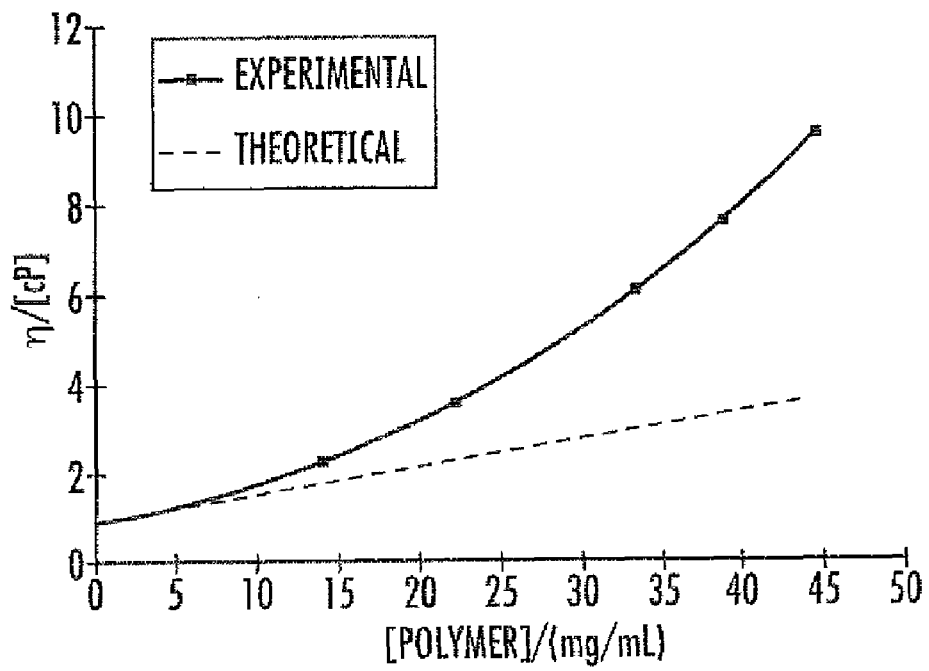
FIG. 4 shows the following: a) Viscosity responses of 15 mM glucose PBS solution to polymer 1 (2.3% of PAAPBA, from 0 to 45 mg/mL). b) Viscosity profile of polymer 2 (2.9% of PMPBA) solutions to glucose (from 0 to 500 mM). c) Viscosity responses of different polymers (2-5 with the percentage of the PMPBA varied from 2.9%, 4.7%, 8.7% and 0%, respectively) to various glucose concentrations. For polymer 3, the viscosity was out of the detection limit when the glucose concentration is higher than 9 mM. d) Viscosity responses of polymer 3 (44.4 mg/mL, 4.7% of PMPBA) solutions to monosaccharides: glucose, fructose, galactose and mannose; and disaccharides: cellobiose, lactose and sucrose.

The viscosity of the copolymers were measured by Ubbelohde viscometer in 0.12 M NaCl at pH 6.0 at 25° C., such as disclosed in Kuzimenkova, M. V.; Ivanov, A. E.; Galaev, I. Y. Macromol. Biosci. 2006, 6, 170-178, which is incorporated by reference herein to the extent it does not conflict with the present disclosure. The conventional Ubbelohde capillary viscometer was employed to measure the kinematic viscosity property of our polymer solutions at room temperature 25° C., which was converted to viscosity because the polymer solution density was approximately the same as water. In order to make sure of the accuracy of fluid viscosity response, multiple measurements were taken for each data point, where the errors were all within 2% range that may be due to possible temperature fluctuations and human errors (FIG. 4a). After the polymer was dissolved in phosphate buffer saline (PBS, pH 7.4, 150 mM NaCl, 0.05% NaN$_3$) that is mimic the physiological pH conditions, the polymer solution was loaded into the viscometer, followed by addition of different amounts of glucose for varying glucose concentrations. The viscosity values became steady within minutes (data not shown), which showed little variations even after hours, suggesting that the system quickly reached an equilibrium state. This rapid response made the polymer a desirable alternative to Con A for detection of glucose.

According to the formula for polyacrylamide, the weight-average molecular weights ($M_w$) of PAA-ran-PAAPBA polymers were calculated from their intrinsic viscosities:

$$[\eta]=5.31\times10^{-3}\times M_w^{0.79}$$

The experimental results were summarized in Table 1.

TABLE 1

Characteristics of polymers prepared in DMSO at 70° C.

| Polymer[a] | Component Molar Ratio AM/monomer[b]/AIBN | Yield | Mw*10$^{-4}$[c] | AAPBA %[d] |
|---|---|---|---|---|
| 1 | 100/2/0.5 | 29% | 8.3 | 2.3% |
| 2 | 100/2/0.25 | 78% | 10.8 | 2.9% |
| 3 | 100/5/0.25 | 43% | 13.0 | 4.7% |
| 4 | 100/8/0.25 | 55% | 5.7 | 8.7% |
| 5 | 100/5/0.25 | 44% | 16.2 | 0% |

[a]Polymers 1-4 are polymers PAA-ran-PAAPBA; 5 is the control polymer PAA-ran-PPAA.
[b]Polymerization co-monomer is AAPBA, except for polymer 5, which is NPAA.
[c]The weight-average molecular weight was measured by viscometry.
[d]The percent composition was calculated by the integration ratio of the aromatic protons to methylene and methine protons using $^1$H NMR spectroscopy.

Since AAPBA is not water soluble, introduction of polyacrylamide segments improved the water solubility of polyAAPBA. Their molecular weights were characterized by viscometric method. The percent composition of AAPBA in the polymer was calculated from the integration ratio in $^1$HNMR spectroscopy.

Viscosity Experiments

All the viscosity experiments were conducted at room temperature. A conventional Ubbelohde capillary viscometer was employed to measure the kinematic viscosity property of our polymer solutions, which was converted to viscosity because the polymer solution density was approximately the same as water. After the copolymer was dissolved in phosphate buffer saline (PBS, pH 7.4, 150 mM NaCl, 0.05% NaN$_3$, 9.0 mL), the polymer solution was loaded into a Ubbelohde viscometer, followed by addition of different amounts of glucose for varying glucose concentrations. The viscosity values became steady within minutes, which showed little variations even after hours, indicating that the system quickly reached an equilibrium state.

Polymer 1 with a variety of concentrations was added to a solution of 15 mM glucose concentration as shown in FIG. 4a. Surprisingly, the viscosity increased parabolically when polymer concentration increased as shown by the experimental curve. Normally, at low polymer concentration range, the solution viscosity should have increased linearly as the theoretical dash line. The deviation shown here could be attributed to the increasing crosslinking of polymer by glucose. At 44.4 mg/mL, the viscosity reached 9.6 cp, which is suitable for a viscometer to measure because the increment of viscosity upon addition of glucose has fallen into the detecting range from 8.7 to 43.4 cp of our MEMS device. Due to the limited solubility of these polymers in PBS buffer, it was difficult to get the solution with a concentration higher than 44.4 mg/mL.

Figure 4B:
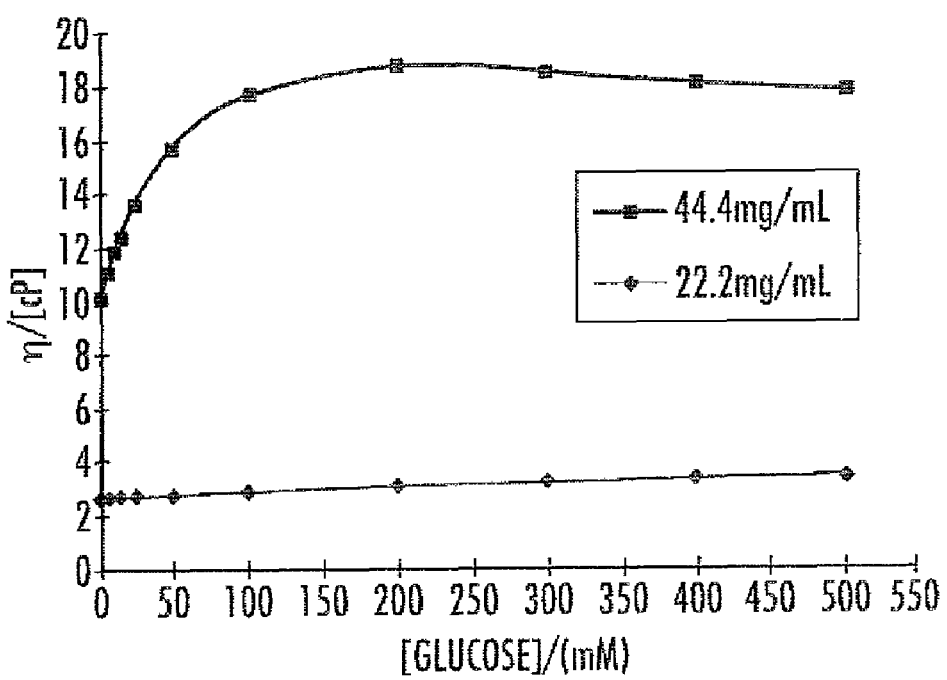

FIG. 4b indicates that at the polymer concentration of 44.4 mg/mL, the viscosity of the solution increased gradually from 10.1 cp (without glucose) to 18.8 cp with the addition of glucose up to a concentration of 200 mM, then slowly declined to 17.8 cp at 500 mM glucose (square data points). When the polymer concentration was 22.2 mg/mL, the viscosity change over glucose concentration from 0 to 500 mM was almost negligible (diamond data points). This indicated that the polymer had a significant response to glucose only at certain concentrations.

Figure 4C:
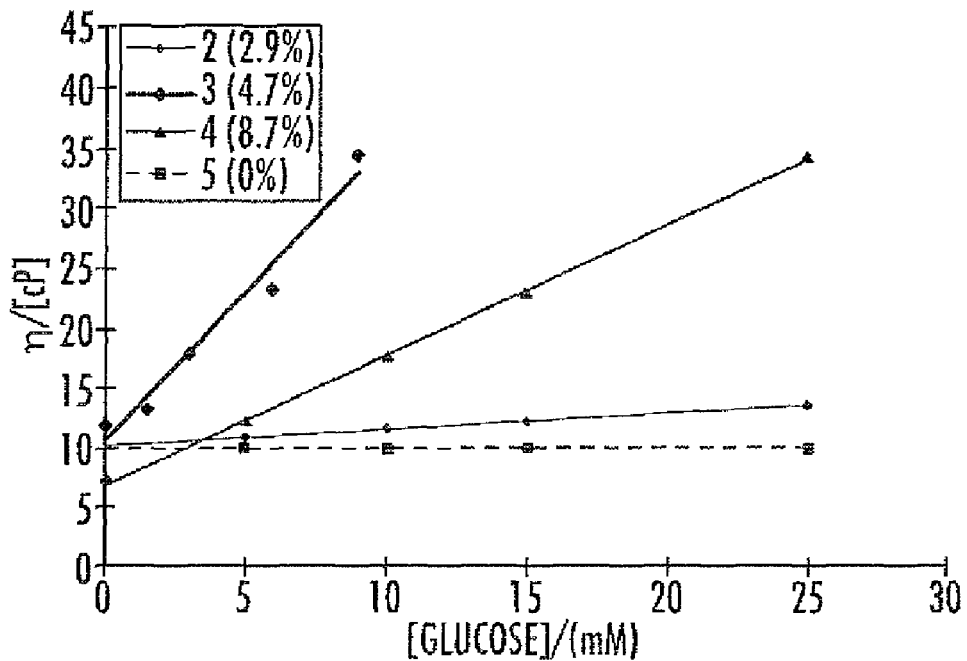

The glucose binding was further tested in response to the composition of the co-polymer. As shown in FIG. 4c, when the glucose concentration increased from 0 to 50 mM, the viscosity of polymer 1 increased gradually, while that of polymer 2 increased linearly from 6.7 to 25.6 cp, which was comparable to that of Con A system used in our previous MEMS device. In the same glucose range, the control polymer 4 without phenylboronic acid group showed no obvious change, even at 500 mM where the small viscosity increment was presumably resulted from increase of glucose concentration alone (not shown). When the glucose concentration increased to 25 mM at which the mixture of polymer 3 turned a little blurry, its viscosity increased sharply from 6.7 to 34.2 cp, suggesting that glucose caused huge amount of crosslinking and agglomerated the polymer at high phenylboronic acid concentration. In addition, it was observed that though the polymers were of various molecular weights, their viscosity response trends were not in the order of molecular weights, but in the percentage of the boronic acid in the polymers, confirming that the crosslinking by glucose generated a much larger impact on viscosity than the polymer itself. It demonstrated that the composition of the polymer played a role in determining its viscosity response, though the molecular weight influenced the viscosity to a relatively minor extent. An enhanced viscosity response was also seen when the polymer molecular weight increased dramatically. The higher the percentage of PAAPBA in the polymer, the more viscous the polymer and glucose mixture is.

Figure 4D:
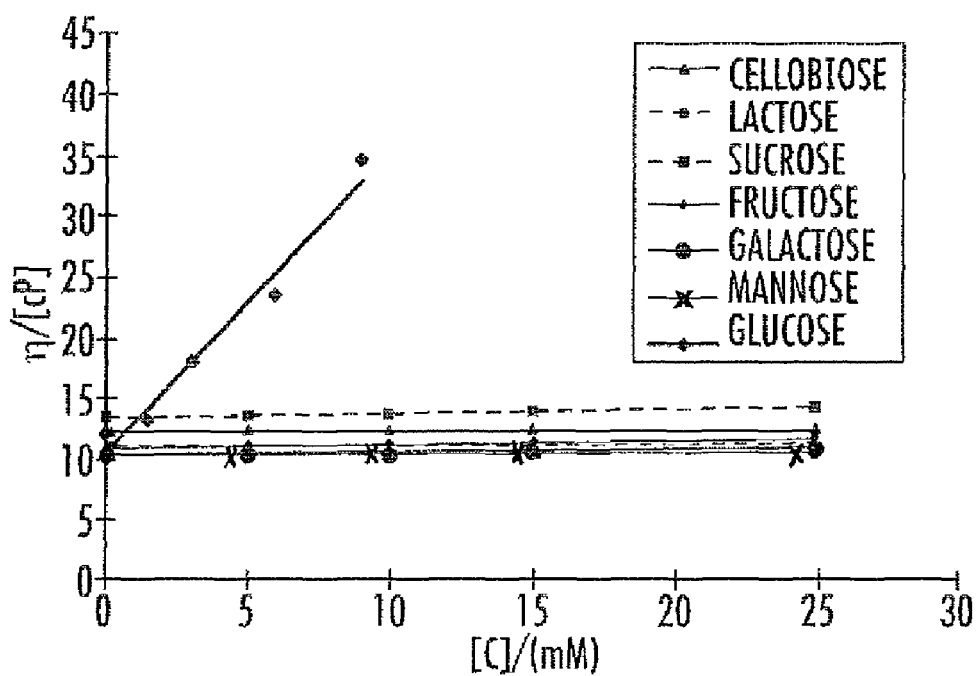

This sensing fluid has shown a high specificity towards glucose. FIG. 4d shows that when the concentration of various monosaccharides increased from 0 to 50 mM, slight viscosity increases were observed for PAA-ran-PAAPBA (polymer 3 in Table 1): 1.1 cp for fructose, 1.7 cp for galactose, all of which were much less than that of glucose, 23.9 cp. It also shows the interactions of different disaccharides including cellobiose, lactose and sucrose with PAA-ran-PAAPBA (polymer 3 in Table 1): 0.5 cp for cellobiose, 0.4 cp for lactose and 0.3 cp for sucrose. When the concentration increased from 0 to 50 mM, slight viscosity increase was also observed for PAA-ran-PAAPBA (polymer 3 in Table 1): 0.5 cp for mannose. Again, no apparent increments of viscosities were observed, indicating that the polymers can not substantially cross-link with those disaccharides.

Reversibility Experiments

Figure 5:
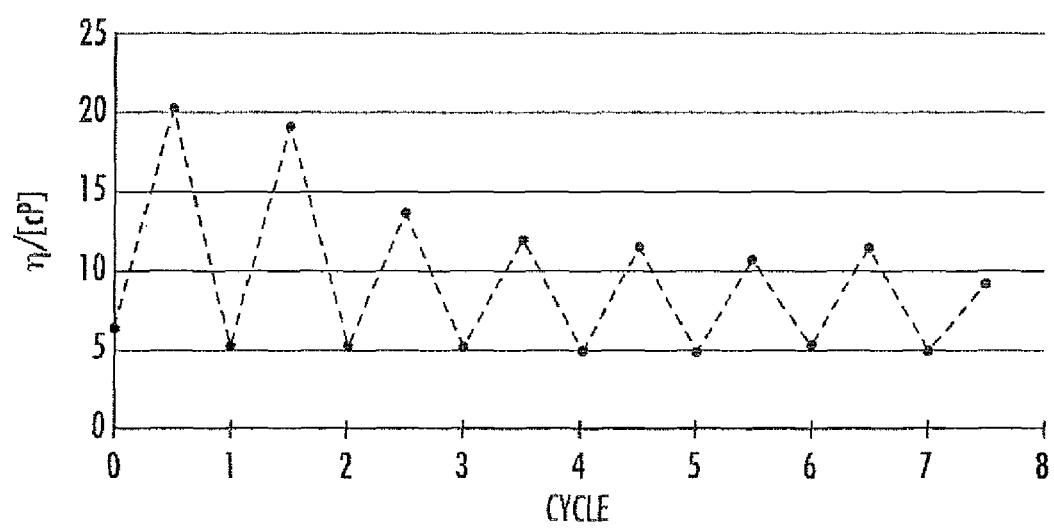
FIG. 5 shows the viscosity response of polymer 3 (31 mg/mL) to glucose (high points) compared to the treatment with 28 mM of glucose (low points). Dialysis against buffer for 12 h except the first run which was in PBS.

Reversibility experiments showed that the response of the fluid to glucose was reversible. The polymer concentration was lowered to 31 mg/mL in order to use glucose concentration around 25 mM. The blank solution showed a viscosity of 6.4 cP in Cycle 1. After addition of glucose, its viscosity was bumped up to 20.4 cP. After dialysis, its viscosity significantly dropped to 5.4 cP, suggesting that removal of glucose led to the dissociation of the crosslinking network and resulted in lower viscosity. Such kind of response was reversible as shown in FIG. 5. Although the increment amplitudes were slightly different which was presumably due to the loss of polymer on the dialysis device, the reproducibility of glucose responses were fully validated overall.

Conclusions

These experiments revealed a completely different sensing mechanism than a Con A system. Previous Con A viscometric affinity glucose sensors were based on the competitive binding of dextran and free glucose to Con A, where the viscosity was provided by the crosslinked Con A and dextran mixture. In this study, the copolymer PAA-ran-PAAPBA showed extremely high specificity toward glucose. When other monosaccharides or disaccharides were tested in the experiments, no viscosity responses were observed. Thus, some sort of crosslinking or structural change among the polymer chains occurs upon contact with glucose. Interactions of phenylboronic acid moieties with amino functionalities in ortho-position of the same phenyl ring enhances the binding of sugars to the boronic acid because of a chelating effect between B and N atoms. However, similar interaction seems weaker between weak Lewis base of amide nitrogen and boron, likely due to the weaker electron donating effect of amide nitrogen. Therefore, it is more likely that sugar binding was augmented by the interaction involving the carbonyl oxygen coordination to the boron open shell as in ortho-carbonyl oxygen and boron in addition to hydrogen bond formation between the N—H group and the oxygen on the boronic acid moiety, which were observed in aliphatic amidoboronic acids. Therefore, the introduction of polyacrylamide can potentially enhance glucose binding via a B—O chelating. In addition, it helped increasing the water solubility of hydrophobic PAAPBA segments. Statistically, there are about twenty hydrophilic acrylamide units per one hydrophobic AAPBA unit on the polymer backbone. When the amphiphilic polymer is dissolved in PBS solution, it would behave like a surfactant. It is believed that sensing proceeds via the synergistic interaction between the phenylboronic acid moieties on the polymer backbone and glucose at the ratio of two to one (Scheme 1), which induces the crosslinking that causes an increase in the solution viscosity. This whole crosslinking process is completely reversible because of the reversibility of the formation of borate esters. When the environmental glucose concentration decreases, the equilibrium would shift to left according to Le Chatelier law. Dissociation of the glucose would break the crosslinked network and reduce the viscosity.

It is well-known that temperature has strong impact on the fluid viscosity. We have observed that the sensing fluid viscosity decreased when temperature increased because of the high molecule mobility, however still maintained sufficient sensing capability. At physiological temperature, lower fluid viscosity will be expected.

In conclusion, a novel glucose selective polymeric sensing fluid based on direct binding was successfully developed. The polymer was easy to be prepared through free radical polymerization. This sensing fluid eliminated the usage of Dextran, simplifying the sensing system and lowering the cost. Its sensitivity to glucose was strongly dependent on the polymer molecular weight and percent composition of boronic acid monomer in copolymer and the polymer concentration. Through proper adjustment of the molecular weight and percent composition of the boronic acid segment in the polymer and the polymer concentration, the sensing fluid was able to detect and differentiate glucose from other monosaccharides and disaccharides. Furthermore, the binding of the polymer with glucose showed good reversibility. Unlike proteins, synthetic polymers are more stable for applications under physiological conditions and do not require any activation metal ions (unlike Con A), therefore, they can be used under different hysiological environments.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method for detecting and differentiating the presence of glucose from other monosaccharides and disaccharides in a sample, the method comprising exposing a polymeric sensing fluid of a viscometric sensor device to the sample, wherein the polymeric sensing fluid comprises a polymer having an acrylic polymeric backbone with a plurality of boronic acid moieties attached, wherein the polymer comprises poly(acrylamide-ran-3-acrylamidophenylboronic acid) formed by polymerizing N-3-acrylamidophenylboronic acid and acrylamide in the presence of 2,2'-azobisisobutyronitrile, and wherein the poly(acrylamide-ran-3-acrylamidophenylboronic acid) comprises N-3-acrylamidophenylboronic acid monomer from about 0.1% to about 10% by mole of the poly(acrylamide-ran-3-acrylamidophenylboronic acid), and measuring a viscosity increase in the polymeric sensing fluid using the viscometric sensor device, thereby differentiating and detecting the presence of glucose from other monosaccharides and disaccharides in the sample.

2. The method of claim 1, wherein the poly(acrylamide-ran-3-acrylamidophenylboronic acid) comprises the N-3-acrylamidophenylboronic acid monomer from about 0.5% to about 8% by mole of the poly(acrylamide-ran-3-acrylamidophenylboronic acid).

3. The method of claim 1, wherein the poly(acrylamide-ran-3-acrylamidophenylboronic acid) comprises the N-3-acrylamidophenylboronic acid monomer from about 1% to about 6% by mole of the poly(acrylamide-ran-3-acrylamidophenylboronic acid).

4. The method of claim 1, wherein the poly(acrylamide-ran-3-acrylamidophenylboronic acid) comprises the N-3-acrylamidophenylboronic acid monomer from about 2% to about 5% by mole of the poly(acrylamide-ran-3-acrylamidophenylboronic acid).

5. The method of claim 1, wherein the poly(acrylamide-ran-3-acrylamidophenylboronic acid) comprises acrylamide monomer from about 90% to about 99.9% by mole of the poly(acrylamide-ran-3-acrylamidophenylboronic acid).

6. The method of claim 1, wherein the poly(acrylamide-ran-3-acrylamidophenylboronic acid) comprises acrylamide monomer from about 92% to about 99.5% by mole of the poly(acrylamide-ran-3-acrylamidophenylboronic acid).

7. The method of claim 1, wherein the poly(acrylamide-ran-3-acrylamidophenylboronic acid) comprises acrylamide monomer from about 94% to about 99% by mole of the poly(acrylamide-ran-3-acrylamidophenylboronic acid).

8. The method of claim 1, wherein the 2,2'-azobisisobutyronitrile is present in the poly(acrylamide-ran-3-acrylamidophenylboronic acid) from about 0.1% to about 1% of the molar amount of the N-3-acrylamidophenylboronic acid monomer.

* * * * *